United States Patent [19]
Draper

[11] Patent Number: 5,747,510
[45] Date of Patent: May 5, 1998

[54] PHARMACEUTICAL UNIT DOSAGE FORMULATIONS

[75] Inventor: Michael W. Draper, Carmel, Ind.

[73] Assignee: Eli Lilly and Company, Indianapolis, Ind.

[21] Appl. No.: 788,984

[22] Filed: Jan. 27, 1997

Related U.S. Application Data

[60] Continuation of Ser. No. 422,417, Apr. 14, 1995, Pat. No. 5,641,790, which is a division of Ser. No. 205,012, Mar. 2, 1994, Pat. No. 5,478,847.

[51] Int. Cl.$^6$ ............. A61K 31/44; C07D 409/00
[52] U.S. Cl. ............. 514/333; 546/202; 549/51
[58] Field of Search ............. 514/333; 546/202; 549/51

[56] References Cited

U.S. PATENT DOCUMENTS

| | | |
|---|---|---|
| 4,133,814 | 1/1979 | Jones et al. |
| 4,380,635 | 4/1983 | Peters |
| 4,418,068 | 11/1983 | Jones |
| 5,075,321 | 12/1991 | Schreiber |
| 5,393,763 | 2/1995 | Black et al. |
| 5,464,845 | 11/1995 | Black et al. |
| 5,641,790 | 6/1997 | Draper |

FOREIGN PATENT DOCUMENTS

| | | |
|---|---|---|
| WO93/10113 | 5/1993 | WIPO |
| WO93/1074 | 6/1993 | WIPO |

OTHER PUBLICATIONS

U.S. application No. 07/920,933, Black et al., filed Jul. 28, 1992.
U.S. application No. 07/995,222, Black et al., filed Dec. 22, 1992.
U.S. application No. 08/035,121, Black et al., filed Mar. 19, 1993.
U.S. application No. 08/082,218, Cullinan et al., filed Jun. 24, 1993.
U.S. application No. 08/096,480, Hock, filed Jul. 22, 1993.
U.S. application No. 08/112,012, Dodge et al., filed Aug. 15, 1993.
U.S. application No. 08/111,796, Dodge et al., filed Aug. 25, 1993.
U.S. application No. 08/081,610, Yang, filed Jun. 21, 1993.
U.S. application No. 08/138,643, Black et al., filed Oct. 15, 1993.
U.S. application No. 08/138,642, Black et al., filed Oct. 15, 1993.
U.S. application No. 08/170,945, Jones et al., filed Dec. 21, 1993.
Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti-estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti-Estrogen, Simulates the Effects of Estrogen in Inhibiting Bone Resorption Through Regulating TGFB–3 Expression in Bone;".Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice." Life Sciences, 26:1980, 1453–1458.
Black et al., "Differential Interaction of Antiestrogens with Cytosol Estrogen Receptors." Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.

(List continued on next page.)

Primary Examiner—Paul J. Killos
Attorney, Agent, or Firm—James J. Sales

[57] ABSTRACT

A method of inhibiting bone loss or resorption, or lowering serum cholesterol, comprising administering to a human in need thereof a compound having the formula

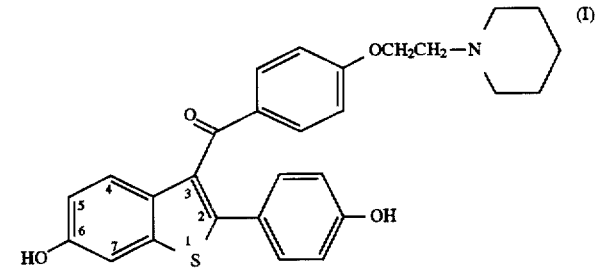

or a pharmaceutically acceptable salt or solvate thereof, in a low dosage amount. Also encompased by the invention is a a pharmaceutical formulation in unit dosage form comprising, per unit dosage, a low dosage amount.

14 Claims, No Drawings

OTHER PUBLICATIONS

Black, L.J. "Biological Actions and Binding Properites of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983, 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22:1979, 962–966.

Black et al., Antiestrogens 2. Structure Activity Studies in a Series of 3–Aroyl–2–arylbenzo[b]thiophene Derivatives Leading to [6–Hydroxy–2(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Cypriani, B. et al., "Effect of Estradiol and Antiestrogens on Cholesterol Biosynthesis in Hormone–Dependent and Independent Breast Cancer Cell Lines," *Biochimica et Biophysica Act*, 972(1988) 167–178.

Cypriani, B., et al., "Role of Estrogen Receptors and Antiestrogen Binding Sites in an Early Effect of Antiestrogens, the Inhibition of Cholesterol Biosynthesis," *J. Steroid Biochem* 31(5) pp. 763–771, 1988.

U.S. application No. 08/479,585, Gibson et al., filed Jun. 7, 1995.

U.S. application No. 08/422,417, Draper, filed Apr. 15, 1995.

PHARMACEUTICAL UNIT DOSAGE FORMULATIONS

This application is a continuation of application Ser. No. 08/422,417 filed Apr. 14, 1995, now U.S. Pat. No. 5,641,790 which is a divisional of application Ser. No. 08/205,012 filed Mar. 2, 1994 now U.S. Pat. No. 5,478,847.

FIELD OF THE INVENTION

This invention relates to methods for inhibiting bone loss and lowering serum cholesterol using low dosage amounts of particular 2-phenyl-3-aroylbenzothiophenes.

BACKGROUND OF THE INVENTION

I. Bone Loss

The current major diseases or conditions of bone which are of public concern include post-menopausal osteoporosis, ovariectomy patients, senile osteoporosis, patients undergoing long-term treatment of corticosteroids, side effects from glucocorticoid or steroid treatment, patients suffering from Cushings's syndrome, gonadal dysgensis, periarticular erosions in rheumatoid arthritis, osteoarthritis, Paget's disease, osteohalisteresis, osteomalacia, hypercalcemia of malignancy, osteopenia due to bone metastases, periodontal disease, and hyperparathyroidism. All of these conditions are characterized by bone loss, resulting from an imbalance between the degradation of bone (bone resorption) and the formation of new healthy bone. This turnover of bone continues normally throughout life and is the mechanism by which bone regenerates. However, the conditions stated above will tip the balance towards bone loss such that the amount of bone resorbed is inadequately replaced with new bone, resulting in net bone loss.

One of the most common bone disorders is post-menopausal osteoporosis which affects an estimated 20 to 25 million women in the United States alone. Women after menopause experience an increase in the rate of bone turnover with resulting net loss of bone, as circulating estrogen levels decrease. The rate of bone turnover differs between bones and is highest in sites enriched with trabecular bone, such as the vertebrae and the femoral head. The potential for bone loss at these sites immediately following menopause is 4–5% per year. The resulting decrease in bone mass and enlargement of bone spaces leads to increased fracture risk, as the mechanical integrity of bone deteriorates rapidly.

At present, there are 20 million people with detectable vertebral fractures due to osteoporosis and 250,000 hip fractures per year attributable to osteoporosis in the U.S. The latter case is associated with a 12% mortality rate within the first two years and 30% of the patients will require nursing home care after the fracture. Therefore, bone disorders are characterized by a noticeable mortality rate, a considerable decrease in the survivor's quality of life, and a significant financial burden to families.

Essentially all of the conditions listed above would benefit from treatment with agents which inhibit bone resorption. Bone resorption proceeds by the activity of specialized cells called osteoclasts. Osteoclasts are unique in their ability to resorb both the hydroxyapatite mineral and organic matrix of bone. They are identical with the cartilage resorbing cells, previously termed chondroclasts. It is for this reason that potent inhibitors of osteoclastic bone resorption will also inhibit the cell-mediated degradation of cartilage observed in rheumatoid arthritis and osteoarthritis.

Therapeutic treatments to impede net bone loss include the use of estrogens. Estrogens have been shown clearly to arrest the bone loss observed after menopause and limit the progression of osteoporosis; but patient compliance has been poor because of estrogen side-effects. These side effects include resumption of menses, mastodynia, increase in the risk of uterine cancer, and possibly an increase in the risk of breast cancer.

Alternatively, calcitonin has been used to treat osteoporotic patients. Salmon calcitonin has been shown to directly inhibit the resorption activity of mammalian osteoclasts and is widely prescribed in Italy and Japan. However, calcitonins are prohibitively expensive to many and appear to be short-lived in efficacy. That is, osteoclasts are able to "escape" calcitonin inhibition of resorption by down-regulating calcitonin receptors. Therefore, recent clinical data suggest that chronic treatment with calcitonin may not have long term effectiveness in arresting the post-menopausal loss of bone.

II. Serum Cholesterol

All mammalian cells require cholesterol as a structural component of their cell membranes and for non-sterol end products. Cholesterol is also required for steroid hormone synthesis. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins have been demonstrated to be a major contributing factor in the development and progression of atherosclerosis.

In mammals, serum lipoprotein is composed of cholesterol together with cholesteryl esters, triglycerides, phospholipids and apoproteins. Serum or plasma lipoprotein is comprised of several fractions. The major fractions or classes of plasma lipoproteins are very low density lipoprotein (VLDL), low density lipoprotein (LDL), intermediate density lipoprotein (IDL), and high density lipoprotein (HDL). These classes differ from one another in size, density and in the relative proportions of triglycerides and cholesteryl esters in the core, and in the nature of the apoproteins on the surface.

In mammals, serum cholesterol is derived from exogenous dietary sources as well as through endogenous synthesis. Endogenous synthesis of cholesterol involves a complex set of enzyme-catalyzed reactions and regulatory mechanisms generally termed the mevalonate pathway. Cells face a complex problem in regulating mevalonate synthesis because cholesterol, the bulk end product of mevalonate metabolism, is derived from plasma low density lipoprotein which enters the cell by receptor-mediated endocytosis, as well as from synthesis within the cell. Each cell must balance these external and internal sources so as to sustain mevalonate synthesis while avoiding sterol over accumulation. This balance is achieved through feedback regulation of at least two sequential enzymes in mevalonate synthesis, 3-hydroxy-3-methylglutaryl coenzyme A (HMG-CoA) synthase and HMG-CoA reductase and also of LDL receptors. In the absence of LDL, mammalian cells maintain high activities of the two enzymes, thereby synthesizing mevalonate for production of cholesterol as well as the non-sterol products. When LDL is present, from exogenous sources, HMG-CoA synthase and reductase activity is repressed and the cells produce smaller amounts of mevalonate for the non-sterol end products.

Abundant evidence indicates that treatment of hyperlipoproteinemia will diminish or prevent atherosclerotic complications. In addition to a diet that maintains a normal body weight and minimizes concentrations of lipids in plasma, therapeutic strategies include elimination of factors that exacerbate hyperlipoproteinemia and the administration of therapeutic agents that lower plasma concentrations of lipoproteins, either by diminishing the production of lipoproteins or by enhancing the efficiency of their removal from plasma.

The most promising class of drugs currently available for the treatment of hypercholesterolemia act by inhibiting HMG-CoA reductase, the rate-limiting enzyme of endogenous cholesterol synthesis. Drugs of this class competitively inhibit the activity of the enzyme. Eventually, this lowers the endogenous synthesis of cholesterol and, by normal homeostatic mechanisms, plasma cholesterol is taken up by LDL receptors to restore the intracellular cholesterol balance.

Relative to other cells in the body, liver cells play a critical role in maintaining serum cholesterol homeostasis by both releasing precursors of LDL and through receptor mediated LDL uptake from the serum. In both man and animal models an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesterol esters, converted into bile acids and released into the bile duct, or enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element, appears to confer this sterol end product repression. This element has been extensively studied (Brown, Goldstein and Russell, U.S. Pat. Nos. 4,745,060 and 4,935,363) and appears to consist of a 16 base pair sequence that occurs 5' of the LDL receptor coding region. The sterol response element can be inserted into genes that normally do not respond to cholesterol, conferring sterol end product repression on the chimeric gene. The exact mechanism of this repression is not understood. There is, however, abundant evidence that polar intermediates in cholesterol biosynthesis and naturally occurring as well as synthetic hydroxysterols repress genes containing the sterol response element.

It has been suggested that a hydroxycholesterol binding protein serves as a receptor. When the receptor is bound to an oxysterol it acts on the sterol response element to control transcription through a mechanism that is similar to the action of members of the steroid hormone receptor super gene family.

In populations where coronary heart disease is a major health problem, the incidence of the disease is markedly lower in women than in men. This is particularly true in younger age groups, such as men and women between 35 and 44 years of age.

Generally, plasma lipoprotein metabolism is influenced by the circulating concentrations of gonadal steroids. Changes in serum estrogen and androgen concentrations, resulting from alterations in gonadal status or from the administration of exogenous gonadal steroids are associated with changes in serum lipoprotein levels. The changes effected by estrogens and androgens generally support the proposition that sex differences in lipoproteins are due to hormonal differences between men and women.

The generally accepted relationship between gonadal steroids and plasma lipoproteins is that androgens lower HDL concentrations and increase LDL, thus contributing to the low HDL and high LDL levels observed in men when compared to women. Estrogens are held to have opposite effects on lipoproteins; that is, HDL is raised and LDL is lowered. These sex steroid-induced differences in lipoprotein concentrations are thought to contribute to the lower incidence of cardiovascular disease in women compared to men. After the menopause, the protective effect of estrogens in women is lost and the incidence of cardiovascular disease increases towards the male levels. Postmenopausal women who take estrogens generally have lower rates of cardiovascular disease than women of a similar age who do not. Estrogen, particularly when taken orally, lowers plasma levels of LDL and raises those of HDL.

The mechanisms by which estrogen lowers levels of LDL and raises those of HDL are not known. In general, changes in the plasma concentration of a lipoprotein result from changes in the rate of its synthesis or the rate of its catabolism. For example, estrogen may lower LDL levels by increasing the clearance of LDL from plasma, since estrogen increases the number of hepatic LDL receptors in animals.

Although estrogens have beneficial effects on serum LDL, given even at very low levels, long-term estrogen therapy has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience regular bleeding, which is unacceptable to most older women. Furthermore, combining progesterone with estrogen seems to blunt the serum cholesterol lowering effects of estrogen. Concerns over the significant undesirable effects associated with estrogen therapy, support the need to develop alternative therapies for hypercholesterolemia that generates the desirable effects on serum LDL but does not cause undesirable effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors such as the uterus. Therefore, some antiestrogens, such as tamoxifen, are subject to some of the same adverse effects associated with estrogen therapy.

SUMMARY OF THE INVENTION

The invention provides a method of inhibiting bone resorption and bone loss comprising administering to a human in need thereof a compound of the formula

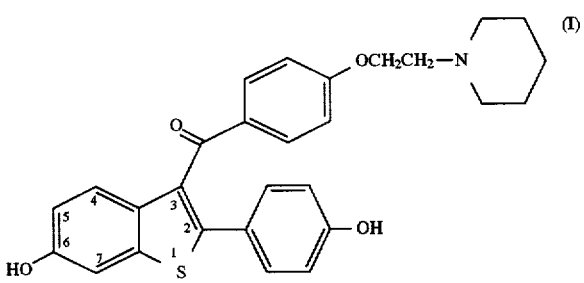

and pharmaceutically acceptable salts and solvates thereof, in an amount of about 50 to about 150 mg/day.

The invention also encompasses a method for lowering serum cholesterol comprising administering a compound of formula I in an amount of about 50 to about 150 mg/day.

The invention also encompases pharmaceutical formulations in dosage unit form, comprising, per dosage with an amount of about 50 to about 150 mg of a compound of formula I.

DESCRIPTION OF THE INVENTION

The current invention concerns the discovery that compounds of formula I are useful for lowering serum cholesterol levels and inhibiting bone resorption and bone loss at dosages of about 50 to about 150 mg/day. The methods provided by this invention are practiced by administering to a human in need thereof a dose of a compound of formula I or a pharmaceutically acceptable salt or solvate thereof in the amount of about 50 to about 150 mg/day, to lower serum cholesterol level, or inhibit bone loss or resorption.

The term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and are well suited to formulation as sustained release dosage forms and the like.

The method of the present invention is useful in men, as well as women. The substantial absence of estrogenic response should allow men to employ the method of the present invention without evidencing the feminizing response of estrogen or estrogen agonists such as gynecomastia. Preferably, however, the methods of the present invention are useful in women, more preferably estrogen deficient women.

The 2-phenyl-3-aroylbenzothiophene compounds that are the active component in the methods of this invention were first developed by C. David Jones and Tulio Suarez as anti-fertility agents (U.S. Pat. No. 4,133,814, issued Jan. 9, 1979). Certain compounds in the group were found to be useful in suppressing the growth of mammary tumors.

Jones later found a group of related compounds to be useful for antiestrogen and antiandrogen therapy, especially in the treatment of mammary and prostatic tumors (U.S. Pat. No. 4,418,068, issued Nov. 29, 1983). One of these compounds, the hydrochloride salt form of the compound of formula I, was clinically tested for a brief time for the treatment of breast cancer. That compound is called raloxifene, formerly keoxifene.

Raloxifene is currently undergoing human clinical trials for use in osteoporsis and lipid lowering. Draper et al. ("Effects of Raloxifene on Biochemical Markers of Bone and Lipid Metabolism in Healthy Post-menopausal Women," Fourth International Symposium on Osteoporosis, Hong Kong, Mar. 29, 1993) discussed certain positive findings of raloxifene's usefulness in inhibiting bone resorption and lowering serum cholesterol. The dosages tested were 200 mg/day and 600 mg/day. As evidenced by EPO Publication EP-A-584952, published Mar. 2, 1994, (corresponding to U.S. application Ser. No. 07/920,933 filed Jul. 28, 1992 (docket X-7947)), the preferred range is listed as 200 mg to 600 mg/day. While this dosing range of 200–600 mg/day does provide sufficient response and is pharmaceutically acceptable, it has now been found that a lower dosage range of raloxifene of about 50 mg/day to about 150 mg/day surprisingly results in providing equivalent benefits as compared to the higher range.

Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally or intravaginaly, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b] thiophene having a 6-hydroxyl group and a 2-(4-hydroxyphenyl) group. The hydroxyl groups of the starting compound are protected, the three position is acylated, and the product deprotected to form the formula I compounds. Examples of the preparation of such compounds are provided in the U.S. patents discussed above.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The dosage range for the invention is about 50 to about 150 mg/day, and preferably 60 to 150 mg/day, and most preferably 60 to 100 mg/day. Particular dosages within the range of the invention are 50, 55, 60, 65, 70, 75, 80, 85, 90, 95, 100, 105, 110, 115, 120, 125, 130, 135, 140, 145, and 150 mg/day.

The compositions are preferably formulated in a unit dosage form, each dosage containing about 50 to about 150 mg, and more preferably the amounts listed above. The term "unit dosage form" refers to physically discrete units, such as tablets and capsules, suitable as unitary dosages, particularly as unitary daily dosages, for human subjects and other mammals, each unit containing a predetermined quantity of active material calculated to produce the desired therapeutic effect, in association with a suitable pharmaceutical excipient.

The term or period of time of administration to a human subject of the dosage of about 50 to about 150 mg/day will vary depending upon severity of the condition, patient health, and related factors which will be decided upon by the attending physician. A course of treatment is expected to be at least for a period of six months, more normally at least one year, and preferably on a continual basis.

Examples of formulations using the dosage range follow:

Formulations
Formulation 1: Gelatin Capsules
Hard gelatin capsules are prepared using the following:

| Ingredient | Quantity (mg/capsule) |
|---|---|
| Raloxifene | 50–150 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of capsule formulations include those shown below:

| Ingredient | Quantity (mg/capsule) |
|---|---|
| Formulation 2: Raloxifene capsule | |
| Raloxifene | 60 |
| Starch, NF | 112 |
| Starch flowable powder | 225.3 |
| Silicone fluid 350 centistokes | 1.7 |
| Formulation 3: Raloxifene capsule | |
| Raloxifene | 75 |
| Starch, NF | 108 |
| Starch flowable powder | 225.3 |
| Silicone fluid 350 centistokes | 1.7 |
| Formulation 4: Raloxifene capsule | |
| Raloxifene | 100 |
| Starch, NF | 103 |
| Starch flowable powder | 225.3 |
| Silicone fluid 350 centistokes | 1.7 |
| Formulation 5: Raloxifene capsule | |
| Raloxifene | 125 |
| Starch, NF | 150 |
| Starch flowable powder | 397 |
| Silicone fluid 350 centistokes | 3.0 |

| Ingredient | Quantity (mg/capsule) |
|---|---|
| Formulation 6: Raloxifene capsule | |
| Raloxifene | 150 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Ingredient | Quantity (mg/tablet) |
|---|---|
| Formulation 7: Tablets | |
| Raloxifene | 60 |
| Cellulose, microcrystalline | 0–650 |
| Silicon dioxide, fumed | 0–650 |
| Stearate acid | 0–15 |
| Formulation 8: Tablets | |
| Raloxifene | 75 |
| Cellulose, microcrystalline | 0–650 |
| Silicon dioxide, fumed | 0–650 |
| Stearate acid | 0 . 15 |
| Formulation 9: Tablets | |
| Raloxifene | 100 |
| Cellulose, microcrystalline | 0–650 |
| Silicon dioxide, fumed | 0–650 |
| Stearate acid | 0–15 |
| Formulation 10: Tablets | |
| Raloxifene | 125 |
| Cellulose, microcrystalline | 0–650 |
| Silicon dioxide, fumed | 0–650 |
| Stearate acid | 0–15 |
| Formulation 11: Tablets | |
| Raloxifene | 150 |
| Cellulose, microcrystalline | 0–650 |
| Silicon dioxide, fumed | 0–650 |
| Stearate acid | 0–15 |

The components are blended and compressed to form tablets.

Alternatively, tablets each containing 50 to 150 mg of active ingredient are made up as follows:

| Ingredient | Quantity (mg/tablet) |
|---|---|
| Formulation 12: Tablets | |
| Raloxifene | 60 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |
| Formulation 13: Tablets | |
| Raloxifene | 75 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |
| Formulation 14: Tablets | |
| Raloxifene | 100 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |
| Formulation 15: Tablets | |
| Raloxifene | 125 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |
| Formulation 16: Tablets | |
| Raloxifene | 150 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 50–150 mg of medicament per 5 mL dose are made as follows:

| Ingredient | Quantity (mg/5 ml) |
|---|---|
| Formulation 17: Suspensions | |
| Raloxifene | 60 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 18: Suspensions | |
| Raloxifene | 75 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 19: Suspensions | |
| Raloxifene | 100 mg |
| Sodium carboxymethyl cellulose | 50 mg |
| Syrup | 1.25 mg |
| Benzoic acid solution | 0.10 mL |
| Flavor | q.v. |

-continued

| Ingredient | Quantity (mg/5 ml) |
|---|---|
| Color | q.v. |
| Purified water to | 5 mL |
| Formulation 20: Suspensions | |
| Raloxifene | 125 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 21: Suspensions | |
| Raloxifene | 150 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following examples illustrate the preparation of the compounds used in the invention.

EXAMPLE 1

6-hydroxy-2-(4-hydroxyphenyl)-3-[4-(2-piperidinoethoxy)benzoyl]benzo[b]thiophene A 4 g. portion of 6-methanesulfonyloxy-2-(4-methanesulfonyloxyphenyl)-3-[4-(2-piperidinoethoxy)benzoyl]benzo[b]thiophene, hydrochloride, was combined with 100 ml. of denatured alcohol and 10 ml. of 5N sodium hydroxide, and stirred under reflux for 1.5 hours under a nitrogen atmosphere. The reaction mixture was then evaporated to dryness under vacuum, and the residue was dissolved in 200 ml. of water and washed with 300 ml. of diethyl ether. The water layer was degassed under vacuum, and then nitrogen was bubbled through it to remove all traces of ether. The mixture was then acidified with 1N hydrochloric acid, and then made basic with excess sodium bicarbonate. The precipitate was collected by filtration and washed with cold water to obtain 2.4 g. of crude product. It was purified on a 2×30 cm. column of silica gel, eluting first with 700 ml. of 5% methanol in chloroform, followed by 1 liter of 10% methanol in chloroform. The impurities came off first, and the product-containing fractions were combined and evaporated under vacuum to obtain 1.78 g. of yellow oil. The oil was dissolved in 6 m. of acetone, seeded and chilled in a freezer to obtain 1.2 g. of purified product, m.p. 143°–147° C. The identity of the product was confirmed as follows:

nmr spectrum (100 mHz in dmso-$d_6$) δ1.20–1.65(6H, m. N($CH_2CH_2$)$_2CH_2$); 2.30–2.45 (4H, m. N($CH_2CH_2$)$_2CH_2$); 2.60 (2H, t, J=6 Hz, O$CH_2CH_2$N); 4.06(2H, t, J=6Hz, O$CH_2CH_2$N); 6.68(2H, d, J=9H, aromatic o to OH); 6.85 (1H,q,$J_{H4-H5}$=9 Hz, $J_{H5-H7}$=2 Hz, H5 of benzothiophene ring); 6.90(2H, d, J=9 Hz, aromatic o to O$CH_2CH_2$N); 7.18 (2H,d,J=9 Hz, aromatic m to OH); 7.25 (1H,d,J=9 z, H4 of benzothiophene ring); 7.66 (2H,d,J=9 Hz, aromatic o to CO); 9.72(2H, broad s, OH). Ultraviolet spectrum in ethanol; $\lambda_{max}$ (ε): 290 nm. (34,000). Electron impact mass spectrum $M_r$ at m/e 473.

EXAMPLE 2

6-hydroxy-2-(4-hydroxyphenyl)-3[-4-(2-piperidinoethoxy)benzoyl]benzo[b]thiophene A 3.6 g. portion of 6-methanesulfonyloxy-2-(4-methanesulfonyloxyphenyl)-3-[4-(2-piperidinoethoxy)benzoyl]benzo[b]thiophene was dissolved in 100 ml. of tetrahydrofuran and 40 ml. of methanol, and 10 ml. of 5N sodium hydroxide was added. The mixture was stirred for 16 hours at ambient temperature, and was then worked up by the procedure of Example 1 above to obtain 3.5 g of a yellow solid. The impure product was purified by column chromatography on silica gel, eluting with a gradient solvent from 5% methanol in chloroform to 30% methanol in chloroform. The product-containing fractions were evaporated to obtain 1.85 g. of oily product, which was recrystallized from acetone to obtain 1.25 g of purified product, m.p. 141°–144° C.

EXAMPLE 3

6-hydroxy-2-(4-hydroxyphenyl)-3[4-(2-piperidinoethoxy)benzoyl]benzo[b]thiophene, hydrochloride Under a nitrogen blanket, a mixture of 3 g. of 4-(2-piperidinoethoxy)benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride were added. The mixture was stirred and allowed to cool to ambient temperature. The precipitate was collected by filtration and washed successively with 30 ml. of water, 40 ml of 25% aqueous tetrahydrofuran, and 35 ml. of water. The solids were then dried at 40° C. under vacuum to obtain 5.05 g. of product, which was identified by nmr.

δ1.7(6H,m, N($CH_2\underline{CH}_2$)$_2\underline{CH}_2$); 2.6–3.1(2H, m, NCH2); 3.5–4.1 (4H, m, N$CH_2$); 4.4(2H, m, O$CH_2$); 6.6–7.4(9H, m, aromatic); 7.7(2H, d, aromatic o to CO); 9.8(2H, m, OH).

Test Results

An 8-week parallel, double-blind, placebo study in approximately 160 healthy post-menopausal women was completed. The doses of raloxifene used in this study were 10, 50, and 200 mg. The 10 mg dose had no significant activity with either bone marker. (See Table I) Because of development over time seen with many bone markers, a raloxifene dose of 50 mg/day will likely be fully active when evaluated during a study of longer duration.

TABLE I

Baseline Values and Mean (±SEM) Group Changes from Baseline to Endpoint in Markers of Bone Metabolism (GGGC)

| Marker | Placebo (n = 42) | Raloxifene 10 mg (n = 42) | Raloxifene 50 mg (n = 42) | Raloxifene 200 mg (n = 41) |
|---|---|---|---|---|
| Serum alkaline phosphatase (U/L) | | | | |
| Baseline | 77.31 (±3.53) | 78.71 (±3.12) | 73.86 (±2.69) | 79.07 (±2.77) |
| Change | −1.10 (±2.08) | 0.21 (±1.56) | −4.78 (±1.52) | −5.93* (±1.48) |
| Serum osteocalcin (ng/mL) | | | | |
| Baseline | 3.94 (±0.21) | 3.86 (±0.19) | 3.65 (±0.21) | 4.21 (±0.21) |
| Change | −0.63 (±0.16) | −0.27 (±0.13) | −0.81 (±0.15) | −1.21* (±0.18) |

Abbreviatons: n = greatest number of subjects tested for any one marker; SEM = standard error of the mean. *Statistically significantly ($p < 0.051$) different from placebo (two-tailed comparison).

Serum lipid levels were affected by raloxifene doses of 50 and 200 mg (Table II). Decreases in LDL cholesterol were observed in raloxifene-treated subjects at 50 mg with a comparable decrease in the 200 mg patients. Raloxifene-treated subjects showed no changes in HDL levels. Statistically significant decreases in HDL:LDL ratios and the total serum cholesterol levels were observed in raloxifene-treated subjects at both the 50 and 200 mg doses.

TABLE II

Baseline Values and Mean (±SEM) Group Changes from Baseline to Endpoint in Serum Lipids (GGGC)

| Variable | Placebo (n = 42) | Raloxifene 10 mg (n = 42) | Raloxifene 50 mg (n = 42) | Raloxifene 200 mg (n = 41) |
|---|---|---|---|---|
| LDL-C (mmol/L) | | | | |
| Baseline | 3.67 (±0.11) | 4.11# (±0.17) | 3.55 (±0.16) | 3.68 (±0.13) |
| Change | 0.02 (±0.08) | 0.05 (±0.10) | −0.23* (±0.06) | −0.17 (±0.07) |
| HDL-C (mmol/L) | | | | |
| Baseline | 1.41 (±0.06) | 1.41 (±0.06) | 1.35 (±0.05) | 1.32 (±0.05) |
| Change | −0.03 (±0.03) | 0.01 (±0.02) | 0.04 (±0.02) | 0.02 (±0.02) |
| HDL-C: LDL-C ratio | | | | |
| Baseline | 0.40 (±0.02) | 0.37 (±0.03) | 0.42 (±0.03) | 0.38 (±0.02) |
| Change | −0.01 (±0.01) | 0.00 (±0.01) | 0.03* (±0.01) | 0.03* (±0.01) |
| Toal cholesterol (mmol/L) | | | | |
| Baseline | 5.69 (±0.12) | 6.18# (±0.19) | 5.82 (±0.21) | 5.71 (±0.14) |
| Change | 0.10 (±0.09) | 0.01 (±0.10) | −0.23* (±0.08) | −0.15 (±0.08) |

Abbreviations: LDL-C = low-density lipoprotein cholesterol; HDL-C = high-density lipoprotein cholesterol; n = greatest number of subjects tested for any one marker; SEM = standard error of the mean.
Statistically significantly ($p < 0.050$) larger than all other treatments (two-tailed comparison).
*Statistically significantly ($p < 0.050$) different from placebo (two-tailed comparison).

I claim:

1. A pharmaceutical formulation in daily dosage unit form comprising, per daily dosage unit, an amount within the range of about 55 to about 150 mg of a compound of formula I

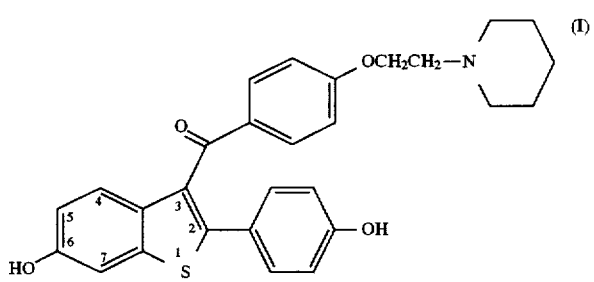

or a pharmaceutically acceptable salt or solvate thereof, said formulation in dosage unit form being adapted for oral administration in the form of a capsule or tablet.

2. A pharmaceutical formulation of claim 1 in a form adapted for administration to inhibit bone loss.

3. A pharmaceutical formulation of claim 1 in a form adapted for administration to lower serum cholesterol or.

4. A pharmaceutical formulation of claim 1 in the form of a capsule.

5. A pharmaceutical formulation of claim 1 in the form of a tablet.

6. A pharmaceutical formulation of claim 1 in the form of a suspension.

7. A pharmaceutical formulation of claim 1 wherein the dosage unit comprises 60 mg of a compound of formula I.

8. A pharmaceutical formulation of claim 1 wherein the dosage unit comprises 75 mg of a compound of formula I.

9. A pharmaceutical formulation of claim 1 wherein the dosage unit comprises 100 mg of a compound of formula I.

10. A pharmaceutical formulation of claim 1 wherein the dosage unit comprises 125 mg of a compound of formula I.

11. A pharmaceutical formulation of claim 1 wherein the dosage unit comprises 150 mg of a compound of formula I.

12. A pharmaceutical formulation of claim 1 wherein said formulation is in the form of a capsule.

13. A pharmaceutical formulation of claim 12 wherein the dosage unit comprises 60 mg of a compound of formula I.

14. A pharmaceutical formulation of claim 12 wherein said formulation is adapted for inhibiting bone loss or bone resorption, or lowering serum lipid levels.

* * * * *